US010765296B2

(12) United States Patent
Koshika (10) Patent No.: US 10,765,296 B2
(45) Date of Patent: Sep. 8, 2020

(54) SCANNING ENDOSCOPE SYSTEM (71) Applicant: OLYMPUS CORPORATION, Tokyo (JP)

(72) Inventor: Soichiro Koshika, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 385 days.

(21) Appl. No.: 15/837,545

(22) Filed: Dec. 11, 2017

(65) Prior Publication Data

US 2018/0110400 A1    Apr. 26, 2018

Related U.S. Application Data

(63) Continuation of application No. PCT/JP2016/060447, filed on Mar. 30, 2016.

(30) Foreign Application Priority Data

Jul. 7, 2015 (JP) ................................ 2015-136385

(51) Int. Cl.
*A61B 1/00* (2006.01)
*G02B 26/10* (2006.01)
*G02B 23/24* (2006.01)
*G02B 23/26* (2006.01)
*A61B 1/07* (2006.01)

(52) U.S. Cl.
CPC ...... *A61B 1/00009* (2013.01); *A61B 1/00006* (2013.01); *A61B 1/00172* (2013.01); *A61B 1/07* (2013.01); *G02B 23/2469* (2013.01); *G02B 23/26* (2013.01); *G02B 26/101* (2013.01); *G02B 26/103* (2013.01); *A61B 1/00096* (2013.01)

(58) Field of Classification Search
None
See application file for complete search history.

(56) References Cited

U.S. PATENT DOCUMENTS

2015/0338646 A1    11/2015 Innami

FOREIGN PATENT DOCUMENTS

| EP | 2952947 A1 | 12/2015 |
|----|------------|---------|
| JP | 2010501246 A | 1/2010 |
| JP | 2014145942 A | 8/2014 |
| WO | 2008024101 A1 | 2/2008 |
| WO | 2014119288 A1 | 8/2014 |

OTHER PUBLICATIONS

International Search Report dated Jun. 21, 2016 issued in PCT/JP2016/060447.

*Primary Examiner* — Timothy J Neal
(74) *Attorney, Agent, or Firm* — Scully, Scott, Murphy & Presser, P.C.

(57) ABSTRACT

A scanning endoscope system includes an optical fiber configured to guide illumination light, and to emit the illumination light from an end portion, an actuator configured to shift an irradiation position of the illumination light, by swinging the end portion of the optical fiber, a drive signal generator configured to generate and supply a drive signal for driving the actuator, a current measurement section configured to measure, as a current measurement value, a current value of the drive signal supplied to the actuator, and a scan control section configured to perform control such that an amplitude value of the drive signal is switched, and to switch a threshold for detecting the current measurement value from a first threshold to a second threshold, when detecting that the current measurement value gradually changes and reaches the first threshold.

8 Claims, 5 Drawing Sheets

SCANNING ENDOSCOPE SYSTEM

CROSS REFERENCE TO RELATED APPLICATION

This application is a continuation application of PCT/JP2016/060447 filed on Mar. 30, 2016 and claims benefit of Japanese Application No. 2015-136385 filed in Japan on Jul. 7, 2015, the entire contents of which are incorporated herein by this reference.

BACKGROUND OF THE INVENTION

1. Field of the Invention

The present invention relates to a scanning endoscope system, and more particularly, to a scanning endoscope system configured to scan an object, and to acquire an image.

2. Description of the Related Art

With regard to endoscopes in a medical field, to reduce a burden on a subject, various techniques for reducing a diameter of an insertion section to be inserted into a body cavity of the subject have been proposed. As an example of such techniques, a scanning endoscope is known which does not have a solid-state image pickup device at a portion corresponding to the insertion section.

More specifically, a system provided with a scanning endoscope is configured to transmit illumination light emitted by a light source through an optical fiber for illumination, to two-dimensionally scan an object along a predetermined scan path by causing an actuator, which is configured to swing a distal end portion of the optical fiber for illumination, to vibrate, to receive return light from the object by an optical fiber for light reception, and to generate an image of the object based on the return light received by the optical fiber for light reception. As a system having a similar configuration to the system, an optical fiber scanning system disclosed in Japanese Patent Application Laid-Open Publication No. 2010-501246 is known, for example.

SUMMARY OF THE INVENTION

A scanning endoscope system according to an aspect of the present invention includes an optical fiber configured to guide illumination light supplied from a light source section, and to emit the illumination light from an end portion, an actuator configured to shift an irradiation position of the illumination light emitted through the optical fiber, by swinging the end portion of the optical fiber, a drive signal generator configured to generate and supply a drive signal for driving the actuator, a current measurement section configured to measure, as a current measurement value, a current value of the drive signal supplied from the drive signal generator to the actuator, and a scan control section configured to control the drive signal generator such that an amplitude value of the drive signal is switched from a first amplitude value to a second amplitude value different from the first amplitude value, and to switch a threshold for detecting the current measurement value from a first threshold to a second threshold different from the first threshold, when detecting that the current measurement value gradually changes and reaches the first threshold.

DETAILED DESCRIPTION OF THE PREFERRED EMBODIMENT

Hereinafter, an embodiment of the present invention will be described with reference to the drawings.

Figure 1:
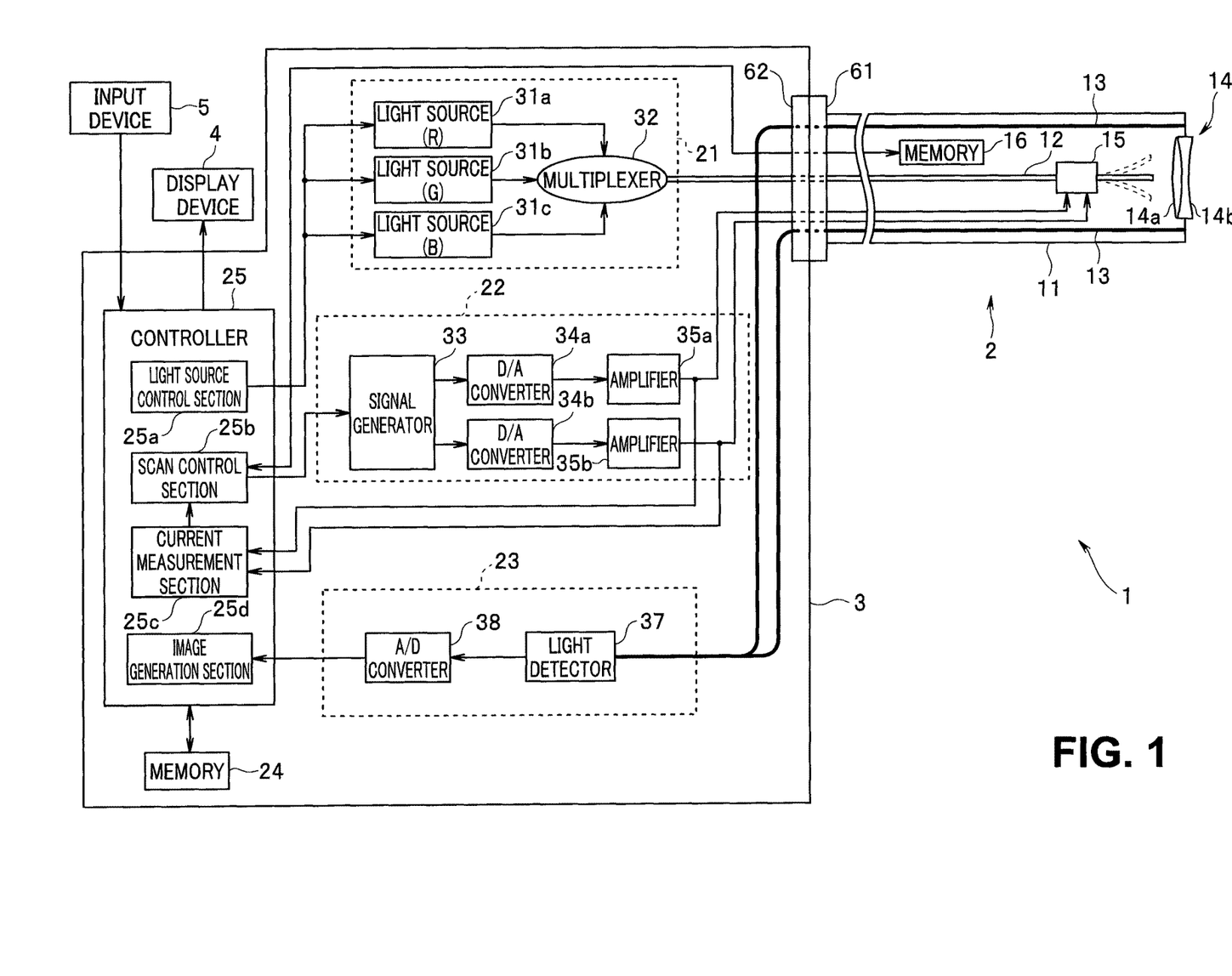
FIG. 1 is a diagram showing a configuration of main parts of a scanning endoscope system according to an embodiment.

FIGS. 1 to 7 relate to an embodiment of the present invention. FIG. 1 is a diagram showing a configuration of main parts of a scanning endoscope system according to the embodiment.

As shown in FIG. 1, a scanning endoscope system 1 includes a scanning endoscope 2, which is inserted into a body cavity of a subject, a main body device 3 to which the scanning endoscope 2 can be connected, a display device 4, which is connected to the main body device 3, and an input device 5, which allows input of information and issuance of an instruction to the main body device 3, for example.

The scanning endoscope 2 includes an insertion section 11, which is formed to have an elongated shape that can be inserted into a body cavity of a subject.

A connector section 61 configured to detachably connect the scanning endoscope 2 to a connector receiving section 62 of the main body device 3 is provided at a proximal end portion of the insertion section 11.

Although not shown, an electrical connector device configured to electrically connect the scanning endoscope 2 and the main body device 3 is provided inside the connector section 61 and the connector receiving section 62. Moreover, although not shown, an optical connector device configured to optically connect the scanning endoscope 2 and the main body device 3 is provided inside the connector section 61 and the connector receiving section 62.

Each of an illumination fiber 12, which is an optical fiber configured to guide illumination light supplied from a light source unit 21 of the main body device 3 and to emit the illumination light from an emitting end portion, and a light receiving fiber 13 including at least one optical fiber configured to receive return light from an object and to guide the return light to a detection unit 23 of the main body device 3 is inserted through a part, of the inside of the insertion section 11, from the proximal end portion to a distal end portion.

An incident end portion of the illumination fiber 12 including a light incident surface is arranged at a multiplexer 32, which is provided inside the main body device 3. And, the emitting end portion of the illumination fiber 12 including a light emitting surface is arranged near a light incident surface of a lens 14a provided at the distal end portion of the insertion section 11.

An incident end portion of the light receiving fiber 13 including a light incident surface is fixedly arranged at a surrounding of a light emitting surface of a lens 14b, at a distal end surface of the distal end portion of the insertion section 11. And, an emitting end portion of the light receiving fiber 13 including a light emitting surface is arranged at a light detector 37, which is provided inside the main body device 3.

An illumination optical system 14 is configured by including the lens 14a where illumination light which has passed through the light emitting surface of the illumination fiber 12 enters, and the lens 14b, which emits the illumination light which has passed through the lens 14a to an object.

An actuator section 15, which is driven by a drive signal supplied from a driver unit 22 of the main body device 3, is provided at a mid-portion of the illumination fiber 12, on a distal end portion side of the insertion section 11.

Figure 2:
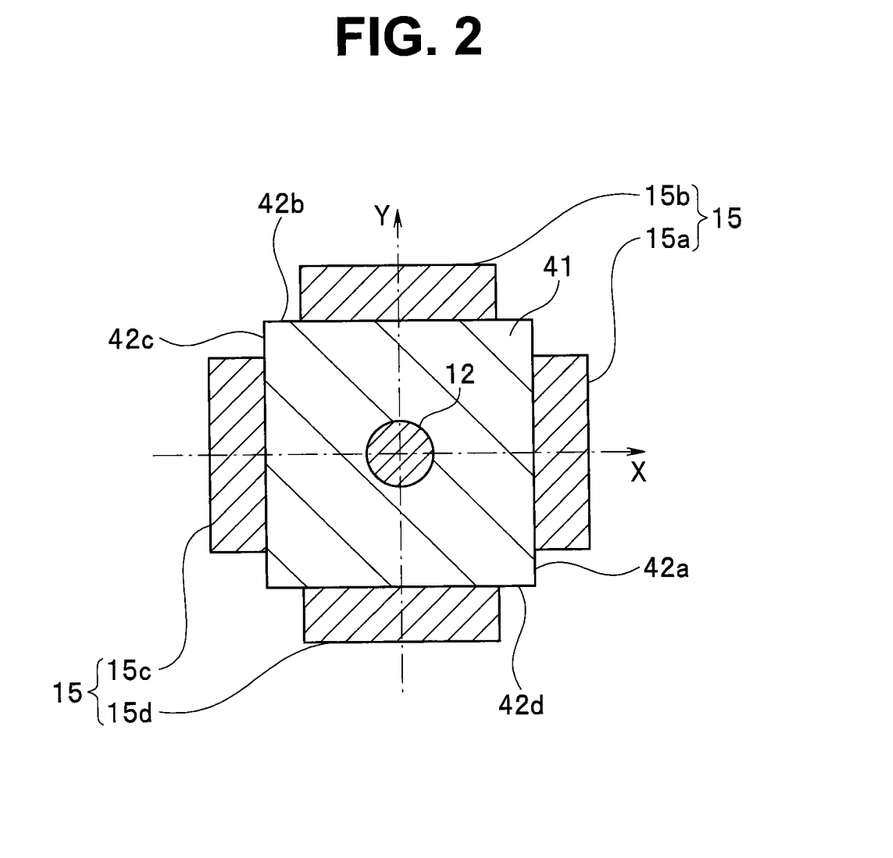
FIG. 2 is a cross-sectional diagram for describing a configuration of an actuator section.

For example, the illumination fiber 12 and the actuator section 15 are arranged in a positional relationship as shown in FIG. 2, for example, at a cross-section perpendicular to a longitudinal axis direction of the insertion section 11. FIG. 2 is a cross-sectional diagram for describing a configuration of the actuator section.

As shown in FIG. 2, a ferrule 41 as a joining member is arranged between the illumination fiber 12 and the actuator section 15. More specifically, the ferrule 41 is formed of zirconia (ceramics) or nickel, for example.

As shown in FIG. 2, the ferrule 41 is formed as a quadrangular prism, and includes side surfaces 42a and 42c, which are perpendicular to an X-axis direction, which is a first axis direction orthogonal to the longitudinal axis direction of the insertion section 11, and side surfaces 42b and 42d, which are perpendicular to a Y-axis direction, which is a second axis direction orthogonal to the longitudinal axis direction of the insertion section 11. Moreover, the illumination fiber 12 is fixedly arranged at a center of the ferrule 41. Note that the ferrule 41 may be formed into a shape other than the quadrangular prism as long as the ferrule 41 has a columnar shape.

For example, as shown in FIG. 2, the actuator section 15 includes a piezoelectric element 15a, which is arranged along the side surface 42a, a piezoelectric element 15b, which is arranged along the side surface 42b, a piezoelectric element 15c, which is arranged along the side surface 42c, and a piezoelectric element 15d, which is arranged along the side surface 42d.

The piezoelectric elements 15a-15d have a polarization direction which is individually set in advance, and are configured to expand or contract according to a drive voltage that is applied by a drive signal supplied from the main body device 3.

That is, the piezoelectric elements 15a and 15c of the actuator section 15 are configured as an X-axis actuator which is capable of swinging the illumination fiber 12 in the X-axis direction by vibrating according to a drive signal that is supplied from the main body device 3. Moreover, the piezoelectric elements 15b and 15d of the actuator section 15 are configured as a Y-axis actuator which is capable of swinging the illumination fiber 12 in the Y-axis direction by vibrating according to a drive signal that is supplied from the main body device 3.

A non-volatile memory 16 is provided inside the insertion section 11, the memory 16 being for storing a current threshold TH1 which is acquired in advance as a current value to be used for operation of a scan control section 25b described later. The current threshold TH1 stored in the memory 16 is read out by a controller 25 of the main body device 3 at a time when the connector section 61 of the scanning endoscope 2 and the connector receiving section 62 of the main body device 3 are connected and power of the main body device 3 is turned on.

The main body device 3 is configured to include the light source unit 21, the driver unit 22, the detection unit 23, a memory 24, and the controller 25.

The light source unit 21 is configured to include a light source 31a, a light source 31b, a light source 31c, and the multiplexer 32.

The light source 31a includes a laser light source, for example, and is configured to emit light in a red wavelength band (hereinafter referred to also as R light) to the multiplexer 32 when emitting light under control of the controller 25.

The light source 31b includes a laser light source, for example, and is configured to emit light in a green wavelength band (hereinafter referred to also as G light) to the multiplexer 32 when emitting light under control of the controller 25.

The light source 31c includes a laser light source, for example, and is configured to emit light in a blue wavelength band (hereinafter referred to also as B light) to the multiplexer 32 when emitting light under control of the controller 25.

The multiplexer 32 is configured to multiplex, and to supply to the light incident surface of the illumination fiber 12, the R light emitted by the light source 31a, the G light emitted by the light source 31b, and the B light emitted by the light source 31c.

The driver unit 22 is configured to generate and supply a drive signal DA for driving the X-axis actuator of the actuator section 15, under control of the controller 25. Furthermore, the driver unit 22 is configured to generate and supply a drive signal DB for driving the Y-axis actuator of the actuator section 15, under control of the controller 25. Moreover, the driver unit 22 is configured by including a signal generator (drive signal generator) 33, D/A converters 34a and 34b, and amplifiers 35a and 35b.

Under control of the controller 25, the signal generator 33 generates, as a first drive control signal for swinging the emitting end portion of the illumination fiber 12 in the X-axis direction, a signal having a waveform as expressed by equation (1) below, for example, and outputs the signal to the D/A converter 34a. Note that in equation (1) below, X(t) indicates a signal level at a time t, Ax indicates an amplitude value not dependent on the time t, and G(t) indicates a predetermined function used for modulation of a sine wave $\sin(2\pi ft)$.

$$X(t) = Ax \times G(t) \times \sin(2\pi ft) \quad (1)$$

Furthermore, under control of the controller 25, the signal generator 33 generates, as a second drive control signal for swinging the emitting end portion of the illumination fiber 12 in the Y-axis direction, a signal having a waveform as expressed by equation (2) below, for example, and outputs the signal to the D/A converter 34b. Note that in equation (2) below, Y(t) indicates a signal level at a time t, Ay indicates an amplitude value not dependent on the time t, G(t) indicates a predetermined function used for modulation of a sine wave $\sin(2\pi ft + \varphi)$, and $\varphi$ indicates a phase.

$$Y(t) = Ay \times G(t) \times \sin(2\pi ft + \varphi) \quad (2)$$

The D/A converter 34a is configured to convert a digital first drive control signal outputted from the signal generator 33 into the drive signal DA, which is an analog voltage signal, and to output the signal to the amplifier 35a.

The D/A converter 34b is configured to convert a digital second drive control signal outputted from the signal generator 33 into the drive signal DB, which is an analog voltage signal, and to output the signal to the amplifier 35b.

The amplifier 35a is configured to amplify the drive signal DA outputted from the D/A converter 34a, and to output the signal to the piezoelectric elements 15a and 15c of the actuator section 15.

The amplifier 35b is configured to amplify the drive signal DB outputted from the D/A converter 34b, and to output the signal to the piezoelectric elements 15b and 15d of the actuator section 15.

Figure 3:
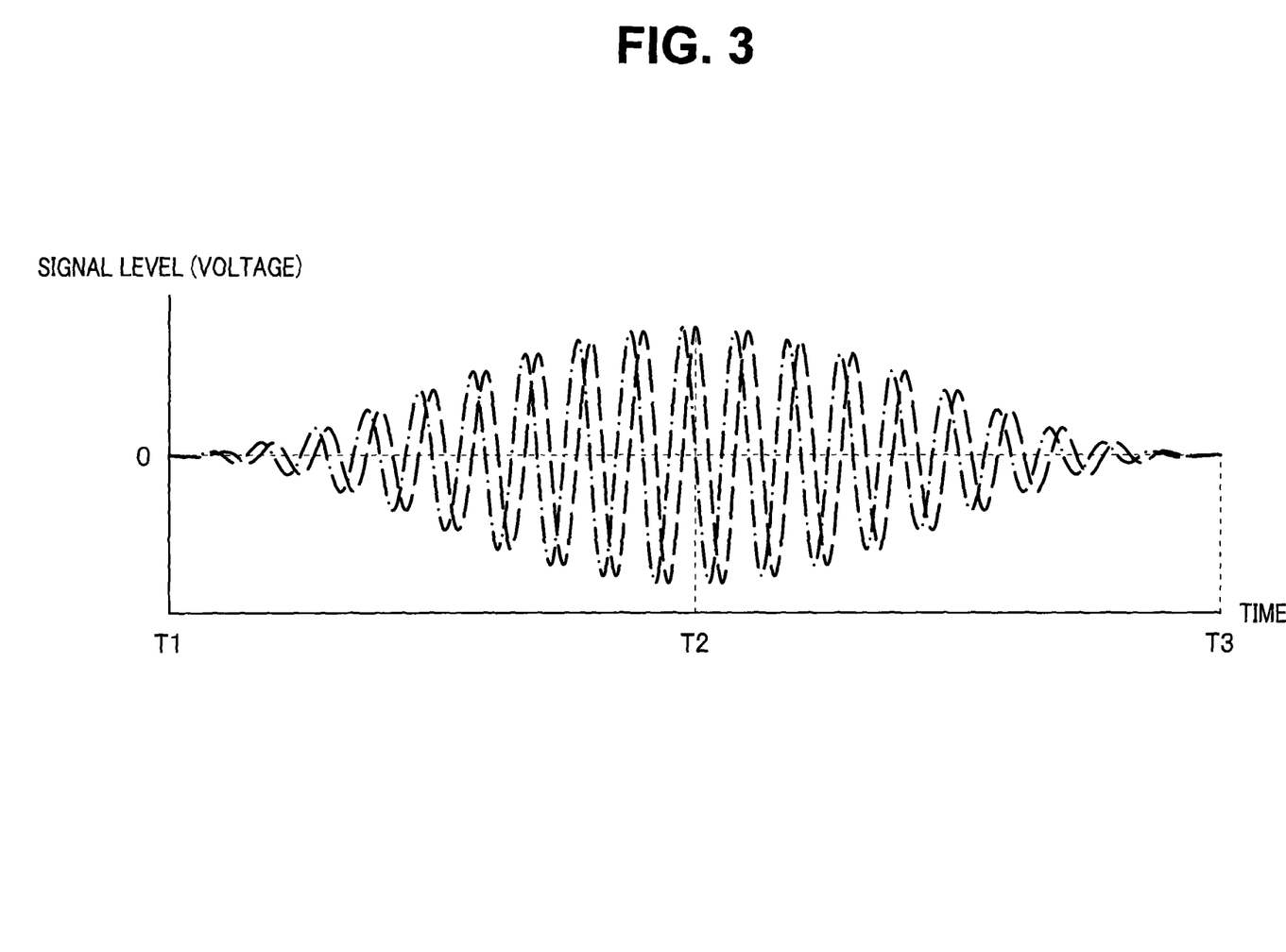
FIG. 3 is a diagram showing respective examples of signal waveforms of drive signals which are supplied to the actuator section.

Here, for example, if $Ax=Ay$ and $\varphi=\pi/2$ are set for equations (1) and (2) above, a drive voltage according to the drive signal DA having a signal waveform as shown by a broken line in FIG. 3 is applied to the piezoelectric elements 15a and 15c of the actuator section 15, and a drive voltage according to the drive signal DB having a signal waveform as shown by a dashed-dotted line in FIG. 3 is applied to the piezoelectric elements 15b and 15d of the actuator section 15. FIG. 3 is a diagram showing respective examples of the signal waveforms of the drive signals which are supplied to the actuator section.

Figure 4:
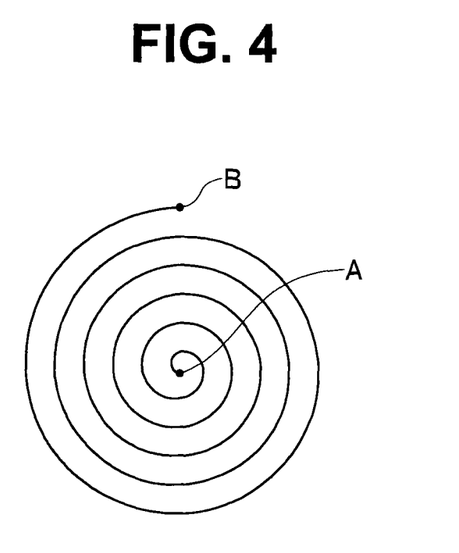
FIG. 4 is a diagram showing an example of a spiral scan path extending from a center point A to an outermost point B.
Figure 5:
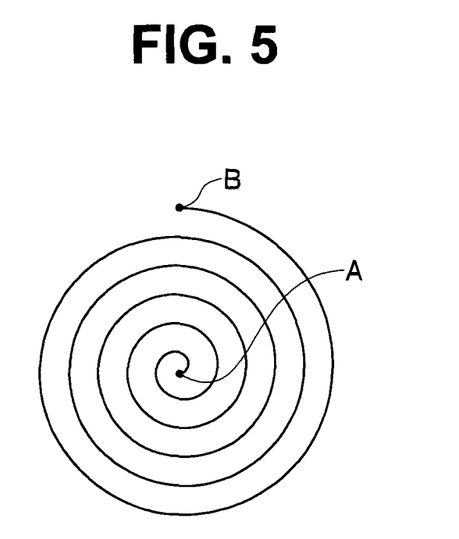
FIG. 5 is a diagram showing an example of a spiral scan path extending from the outermost point B to the center point A.

Moreover, for example, when the drive voltage according to the drive signal DA having the signal waveform as shown by the broken line in FIG. 3 is applied to the piezoelectric elements 15a and 15c of the actuator section 15, and the drive voltage according to the drive signal DB having the signal waveform as shown by the dashed-dotted line in FIG. 3 is applied to the piezoelectric elements 15b and 15d of the actuator section 15, the emitting end portion of the illumination fiber 12 is swung in a spiral manner, and a surface of an object is scanned, due to such swinging, along spiral scan paths as shown in FIGS. 4 and 5. FIG. 4 is a diagram showing an example of a spiral scan path extending from a center point A to an outermost point B. FIG. 5 is a diagram showing an example of a spiral scan path extending from the outermost point B to the center point A.

More specifically, first, at a time T1, illumination light is radiated on a position, on a surface of an object, corresponding to the center point A of irradiation position of illumination light. Then, as signal levels (voltage) of the drive signals DA and DB are increased from the time T1 to a time T2, the irradiation position of the illumination light on the surface of the object is shifted from the center point A, as a start point, toward the outside to draw a first spiral scan path, and when the time T2 is reached, the illumination light is radiated on the outermost point B of the irradiation position of the illumination light on the surface of the object. Then, as the signal levels (voltage) of the drive signals DA and DB are reduced from the time T2 to a time T3, the irradiation position of the illumination light on the surface of the object is shifted from the outermost point B, as a start point, toward the inside to draw a second spiral scan path, and when the time T3 is reached, the illumination light is radiated on the center point A on the surface of the object.

That is, the actuator section 15 is configured to be able to shift the irradiation position of the illumination light which is emitted to an object through the emitting end portion of the illumination fiber 12 along the spiral scan paths shown in FIGS. 4 and 5 by swinging the emitting end portion based on the drive signals DA and DB supplied from the driver unit 22. Moreover, the signal levels of the drive signals DA and DB supplied from the driver unit 22 to the actuator section 15 are maximized at the time T2 or around the time T2.

The detection unit 23 is configured to detect return light received by the light receiving fiber 13 of the scanning endoscope 2, and to generate and output a light detection signal according to intensity of the detected return light. More specifically, the detection unit 23 is configured by including the light detector 37, and an A/D converter 38.

The light detector 37 includes an avalanche photodiode, for example, and is configured to detect intensity of light (return light) that is emitted from the light emitting surface of the light receiving fiber 13, to generate an analog light detection signal according to intensity of the detected light, and to output the signal to the A/D converter 38 in a sequential order.

The A/D converter 38 is configured to convert the analog light detection signal outputted from the light detector 37 into a digital light detection signal, and to output the signal to the controller 25 in a sequential order.

The memory 24 stores, as control information used at the time of control of the main body device 3, information including parameters such as a signal level, a frequency, and a phase difference for identifying a signal waveform in FIG. 3, for example.

The controller 25 is configured by an integrated circuit such as an FPGA (field programmable gate array). Moreover, the controller 25 is configured to be able to detect whether the insertion section 11 is electrically connected to the main body device 3, by detecting a connection state of the connector section 61 at the connector receiving section 62 through a signal line or the like, not shown. Moreover, the controller 25 is configured by including a light source control section 25a, a scan control section 25b, a current measurement section 25c, and an image generation section 25d.

For example, the light source control section 25a is configured to control the light source unit 21 such that R light, G light, and B light are repeatedly emitted in the mentioned order, based on the control information read from the memory 24.

For example, the scan control section 25b is configured to control the driver unit 22 such that a drive signal having a signal waveform as shown in FIG. 3 is generated, based on the control information read from the memory 24.

The scan control section 25b is configured to read the current threshold TH1 stored in the memory 16, when the connector section 61 of the scanning endoscope 2 and the connector receiving section 62 of the main body device 3 are connected and the power of the main body device 3 is turned on, for example. Moreover, the scan control section 25b is configured to perform a process (described later) of acquiring the current threshold TH2, which is a current value greater than the current threshold TH1 read from the memory 16, based on a current value measured by the current measurement section 25c.

For example, when the current measurement value outputted as a measurement result of the current measurement section 25c is detected to have gradually increased and reached the current threshold TH1, the scan control section 25b is configured to perform an operation of amplifying each of the drive signals DA and DB which are supplied from the driver unit 22 to the actuator section 15, and to switch a threshold for detecting the current measurement value from the current threshold TH1 to the current threshold TH2.

For example, when the current measurement value outputted as a measurement result of the current measurement section 25c is detected to have gradually decreased and reached the current threshold TH2, the scan control section 25b is configured to perform an operation of attenuating each of the drive signals DA and DB which are supplied from the driver unit 22 to the actuator section 15, and to switch the threshold for detecting the current measurement value from the current threshold TH2 to the current threshold TH1.

The current measurement section 25c is configured to measure, as a current measurement value MVA, a current value of the drive signal DA which is supplied from the amplifier 35a of the driver unit 22 to the piezoelectric elements 15a and 15c of the actuator section 15, and to output the measured current measurement value MVA to the scan control section 25b. Moreover, the current measurement section 25c is configured to measure, as a current measurement value MVB, a current value of the drive signal DB which is supplied from the amplifier 35b of the driver unit 22 to the piezoelectric elements 15b and 15d of the actuator section 15, and to output the measured current measurement value MVB to the scan control section 25b.

For example, the image generation section 25d is configured to perform a process of generating an observation image of one frame by converting light detection signals sequentially outputted from the detection unit 23 in a period of time from the time T1 to T2 into pixel information and performing raster mapping based on a predetermined mapping table included in the control information read from the memory 24, and of outputting the generated observation image of one frame to the display device 4.

Note that the predetermined mapping table mentioned above is created as a table indicating a correspondence relationship between an output timing of a light detection signal which is outputted from the detection unit 23 in a sequential order and a pixel position which is an application destination of pixel information obtained by converting the light detection signal, for example. Moreover, the image generation section 25d of the present embodiment may read, from the memory 24, another mapping table which is created as a different table from the predetermined mapping table mentioned above, and may convert light detection signals which are sequentially outputted from the detection unit 23 in a period of time from the time T2 to T3 into pixel information and perform raster mapping based on the other mapping table, which has been read, to thereby generate an observation image of one frame and to output the generated observation image of one frame to the display device 4.

The display device 4 includes a monitor or the like, and is configured to be able to display an observation image which is outputted from the main body device 3.

The input device 5 is configured to include a keyboard or a touch panel, for example. Note that the input device 5 may be configured as a separate device from the main body device 3, or may be configured as an interface that is integrated with the main body device 3.

Next, an operation and the like of the scanning endoscope system 1 having a configuration as described above will be described. Note that in the following, for the sake of simplicity, a case where the current measurement values MVA and MVB measured by the current measurement section 25c are a same current measurement value MVK and the current thresholds TH1 and TH2 are used as thresholds for detecting the current measurement value MVK will be described as an example.

First, a description will be given regarding an operation for a case where the current threshold TH2 which was stored in the memory 16 at the time of manufacture of the scanning endoscope 2 is read at the time of use of the scanning endoscope 2 by a user, such as a surgeon.

For example, at the time of manufacture of the scanning endoscope 2, a factory operator connects each part of the scanning endoscope system 1 and switches on the power in a state where the scanning endoscope 2 is placed in an environment where a temperature of the actuator section 15 is at a temperature TE1. Note that the temperature TE1 is a temperature in the range of normal temperature, such as 25 degrees Celsius.

Then, the factory operator instructs the controller 25 to start scanning by the scanning endoscope 2, by operating a scan start switch (not shown) of the input device 5, for example.

When detecting respectively that the scan start switch of the input device 5 is operated, and that the current threshold TH2 to be read from the memory 16 does not exist, the scan control section 25b reads the current threshold TH1 from the memory 16, and controls the signal generator 33 such that each of the drive signal DA for which the amplitude value Ax in equation (1) above is set to Ax1 and the drive signal DB for which the amplitude value Ay in equation (2) above is set to Ay1 is generated. Note that the amplitude values Ax1 and Ay1 are values that are set in advance as amplitude values for a case where the temperature of the actuator section 15 is the temperature TE1, and are included in the control information stored in the memory 24, for example.

After checking that scanning by the scanning endoscope 2 is started, the factory operator gradually increases a temperature around the insertion section 11 of the scanning endoscope 2 such that the temperature of the actuator section 15 reaches a temperature TE2, which is higher than the temperature TE1. Note that the temperature TE2 is a temperature of the actuator section 15 which may be measured when the insertion section 11 of the scanning endoscope 2 is inserted into a body cavity of a subject, such as 30 degrees Celsius.

The scan control section 25b monitors the current measurement value MVK which is outputted from the current measurement section 25c according to supply of the drive signal DA of the amplitude value Ax1 and the drive signal DB of the amplitude value Ay1, while referring to the current threshold TH1.

Here, according to a result of experiment by the applicant, establishment of a linear relationship, as expressed by a linear function in equation (3) below, between the temperature TE of one of the X-axis actuator and the Y-axis actuator of the actuator section 15 and a current value I of a current flowing at the time of supply of the drive signal to the one actuator is confirmed. Note that P and Q in equation (3) below are each a constant.

$$TE = P \times I + Q \qquad (3)$$

That is, according to the relationship expressed by equation (3) above, the current measurement value MVK which is outputted from the current measurement section 25c is linearly changed according to a change in the temperature of the actuator section 15. Accordingly, the scan control section 25b can detect a change in the temperature of the actuator section 15 in a pseudo manner by monitoring a change in the current measurement value MVK outputted from the current measurement section 25c.

Furthermore, the current threshold TH1 corresponds to a current value I that is obtained by performing calculation by substituting TE=30(° C.) in equation (3) above as the value of TE corresponding to the temperature TE2. In other words, the current threshold TH1 is a current value that is measured as the current measurement value MVK at a timing of the temperature of the actuator section 15, to which the drive signal DA of the amplitude value Ax1 and the drive signal DB of the amplitude value Ay1 are being supplied, reaching the temperature TE2.

The scan control section 25b amplifies each of the drive signals DA and DB to be supplied to the actuator section 15, by controlling the signal generator 33 such that the amplitude value of the drive signal DA is switched to Ax2, which is greater than Ax1, and the amplitude value of the drive signal DB is switched to Ay2, which is greater than Ay2, when the current measurement value MVK is detected to have gradually increased and reached the current threshold TH1. Note that the amplitude values Ax2 and Ay2 are values that are set in advance as amplitude values for a case where the temperature of the actuator section 15 is the temperature TE2, and are included in the control information stored in the memory 24, for example. More specifically, the amplitude values Ax2 and Ay2 are set in advance as values which allow, in a case where the temperature of the actuator section 15 is the temperature TE2, scanning of an object with a same angle of view as an angle of view for a case where the temperature of the actuator section 15 is TE1.

The scan control section 25b acquires, as the current threshold TH2, the current measurement value MVK which is outputted from the current measurement section 25c at a timing immediately after switching of the amplitude value of the drive signal DA from Ax1 to Ax2 and switching of the amplitude value of the drive signal DB from Ay1 to Ay2, causes the memory 16 to store the acquired current threshold TH2, and then, controls the image generation section 25d such that a character string or the like for notifying a factory operator of completion of a process regarding acquisition of the current threshold TH2 is displayed on the display device 4. That is, the current threshold TH2 is a current value which is measured as the current measurement value MVK at a timing immediately after switching of the amplitude value of the drive signal DA from Ax1 to Ax2 and switching of the amplitude value of the drive signal DB from Ay1 to Ay2. Note that the scan control section 25b is not limited to store the current threshold TH2 acquired in the above manner in only the memory 16, and may alternatively store the current threshold TH in only the memory 24 or in both the memory 16 and the memory 24, for example.

Before performing observation of an inside of a body cavity of a subject, a user instructs the controller 25 to start scanning by the scanning endoscope 2, by connecting each part of the scanning endoscope system 1 and turning on the power, and then, operating the scan start switch of the input device 5. That is, before the insertion section 11 of the scanning endoscope 2 is inserted into the body cavity of the subject, the temperature of the actuator section 15 is substantially the same as TE1.

When the connector section 61 of scanning endoscope 2 and the connector receiving section 62 of the main body device 3 are connected, and the power of the main body device 3 is turned on, the scan control section 25b reads the control information stored in advance in the memory 24, and the current thresholds TH1 and TH2 stored in advance in the memory 16. Moreover, when detecting operation of the scan start switch of the input device 5, the scan control section 25b controls the signal generator 33 such that each of the drive signal DA of the amplitude value Ax1 and the drive signal DB of the amplitude value Ay1 is generated, based on the control information read from the memory 24.

After checking that scanning by the scanning endoscope 2 is started, the user performs an operation for inserting the insertion section 11 into the body cavity of the subject. Then, in response to such an operation of the user, the temperature around the insertion section 11 of the scanning endoscope 2 is gradually increased, and a size of the current measurement value MVK which is outputted from the current measurement section 25c is gradually increased. Furthermore, the size of the current measurement value MVK which is outputted from the current measurement section 25c is changed as the temperature around the insertion section 11 of the scanning endoscope 2 is changed during observation of a target object inside the body cavity of the subject due to water feeding or the like.

After detecting operation of the scan start switch of the input device 5, the scan control section 25b monitors the current measurement value MVK which is outputted from the current measurement section 25c according to supply of the drive signal DA of the amplitude value Ax1 and the drive signal DB of the amplitude value Ay1, while referring to the current threshold TH1 read from the memory 16.

Then, when the current measurement value MVK is detected to have gradually increased and reached the current threshold TH1, the scan control section 25b performs an operation of amplifying each of the drive signals DA and DB by controlling the signal generator 33 such that the amplitude value of the drive signal DA is switched from Ax1 to Ax2 and the amplitude value of the drive signal DB is switched from Ay1 to Ay2, and of switching the threshold for detecting the current measurement value MVK from the current threshold TH1 to the current threshold TH2.

Furthermore, when the current measurement value MVK is detected to have gradually decreased and reached the current threshold TH2, the scan control section 25b performs an operation of attenuating each of the drive signals DA and DB by controlling the signal generator 33 such that the amplitude value of the drive signal DA is switched from Ax2 to Ax1 and the amplitude value of the drive signal DB is switched from Ay2 to Ay1, and of switching the threshold for detecting the current measurement value MVK from the current threshold TH2 to the current threshold TH1.

Here, according to a result of experiment by the applicant, establishment of a linear relationship, as expressed by a linear function in equation (4) below, between an amplitude value AM corresponding to one of the amplitude value Ax of the drive signal DA and the amplitude value Ay of the drive signal DB and a current value I of a current flowing at the time of supply of the drive signal of the one amplitude value to the actuator section 15 is confirmed. Note that $\alpha$ and $\beta$ in equation (4) below are each a constant.

$$AM = \alpha \times I + \beta \tag{4}$$

That is, according to the relationship expressed by equation (4) above, the current measurement value MVK which is outputted from the current measurement section 25c may be drastically changed according to an amount of change when the amplitude value Ax of the drive signal DA is discretely changed from Ax1 to Ax2 or an amount of change when the amplitude value Ay of the drive signal DB is discretely changed from Ay1 to Ay2, for example.

Figure 6:
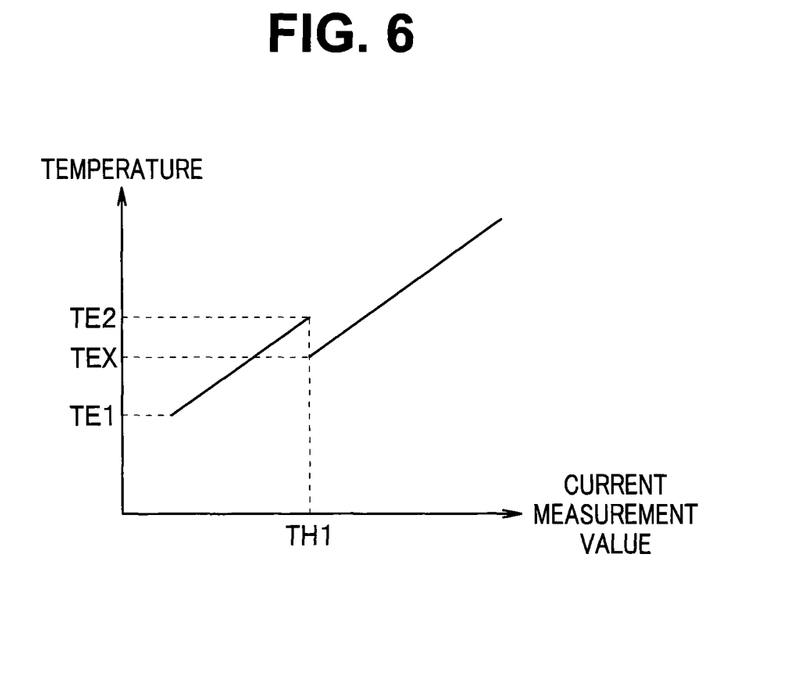
FIG. 6 is a diagram for describing an operation for a case where only a current threshold TH1 is used as a threshold for detecting a current measurement value.

However, the current threshold TH1 is a value that is set by using equation (3) on a premise that the amplitude values Ax and Ay are maintained at constant values. Accordingly, the current threshold TH1 can be used as the threshold for detecting the current measurement value MVK until the temperature of the actuator section 15 reaches the temperature TE2, but cannot be used as the threshold for detecting the current measurement value MVK after a drastic change according to a discrete change in the amplitude value of the drive signal as described above. Accordingly, for example, in the case where only the current threshold TH1 is used as the threshold for detecting the current measurement value MVK, as shown in FIG. 6, a situation occurs where an operation of amplifying the drive signals is performed at a timing of the temperature of the actuator section 15 reaching the temperature TE2 after being gradually increased, but an operation of attenuating the drive signals is not performed until the temperature of the actuator section 15 is gradually reduced and a temperature TEX, which is lower than the temperature TE2, is reached. FIG. 6 is a diagram for describing an operation for a case where only the current threshold TH1 is used as the threshold for detecting the current measurement value.

Figure 7:
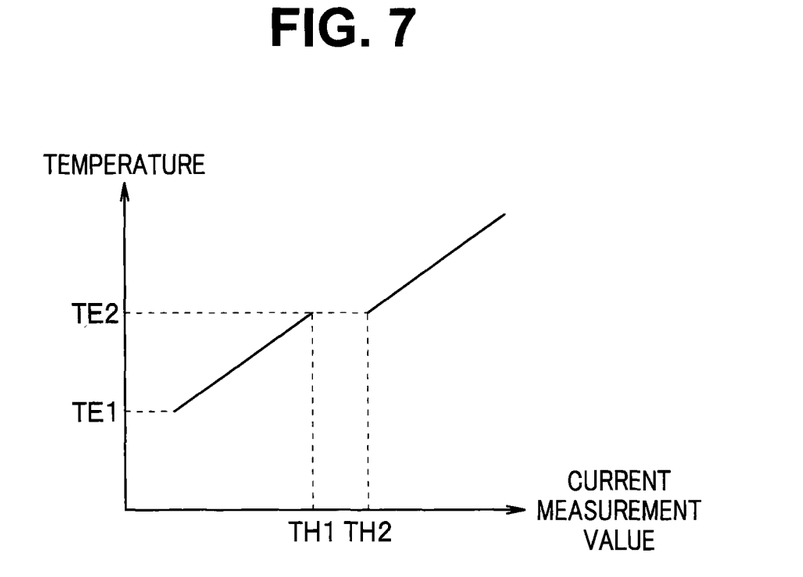
FIG. 7 is a diagram for describing an operation for a case where current thresholds TH1 and TH2 are used as thresholds for detecting a current measurement value.

On the other hand, according to the present embodiment, as shown in FIG. 7, an operation of amplifying the drive signals is performed at a timing of the temperature of the actuator section 15 reaching the temperature TE2 after being gradually increased, and an operation of attenuating the drive signals is performed at a timing of the temperature of the actuator section 15 reaching the temperature TE2 after being gradually reduced, by switching the threshold for detecting the current measurement value MVK from one of the current thresholds TH1 and TH2 to the other threshold at a timing of occurrence of a drastic change in the current measurement value MVK according to a discrete change in the amplitude value of the drive signal as described above, that is, at a timing when the temperature TE2 is reached. FIG. 7 is a diagram for describing an operation for a case where the current thresholds TH1 and TH2 are used as the thresholds for detecting the current measurement value.

Note that the scan control section 25b of the present embodiment may calculate an average value of respective current measurement values which are outputted from the current measurement section 25c within a specific period of time specified, for example, by a period of time when observation images of a predetermined number of frames are generated by the image generation section 25d, and may use the current thresholds TH1 and TH2 as thresholds for detecting the calculated average value. More specifically, for example, when detecting that the average value of respective current measurement values outputted from the current measurement section 25c within the specific period of time has reached the current threshold TH1 after being gradually increased, the scan control section 25b of the present embodiment may perform control such that the amplitude value of the drive signal DA is switched from Ax1 to Ax2 and the amplitude value of the drive signal DB is switched from Ay1 to Ay2, and perform an operation of switching the threshold for detecting the current measurement value MVK from the current threshold TH1 to the current threshold TH2. Furthermore, for example, when detecting that the average value of respective current measurement values outputted from the current measurement section 25c within the specific period of time has reached the current threshold TH2 after being gradually reduced, the scan control section 25b of the present embodiment may perform control such that the amplitude value of the drive signal DA is switched from Ax2 to Ax1 and the amplitude value of the drive signal DB is switched from Ay2 to Ay1, and perform an operation of switching the threshold for detecting the current measurement value MVK from the current threshold TH2 to the current threshold TH1. According to such an operation of the scan control section 25b, occurrence of a situation where the amplitude values of the drive signals are frequently switched due to output, from the current measurement section 25c, of the current measurement value MVK which changes at around the current threshold TH1 or TH2 may be prevented as much as possible, for example.

Moreover, the scan control section 25b of the present embodiment is not limited to instantly switch the amplitude values of the drive signals supplied to the actuator section 15, when the current measurement value MVK reaches one current threshold THX of the current thresholds TH1 and TH2, and may gradually change the amplitude values of the drive signals supplied to the actuator section 15 in a predetermined period of time PT which is set to about 10 seconds, for example, while ignoring a change in the current measurement value MVK during the predetermined period of time PT. Note that in the case of such an operation, if the other current threshold THY of the current thresholds TH1 and TH2 is not reached by the current measurement value MVK immediately after lapse of the predetermined period of time PT, an operation of gradually changing and returning the amplitude values of the drive signals supplied to the actuator section 15 to the amplitude values of the drive signals when the current threshold THX is reached by the current measurement value MVK may be additionally performed. Moreover, according to the operation of the scan control section 25b as described above, a visually unnatural feeling at the time of a display state of an observation image displayed on the display device 4 changing in response to switching of the amplitude values of the drive signals supplied to the actuator section 15 may be reduced, for example.

Furthermore, the scan control section 25b of the present embodiment is not limited to directly acquire, as the current threshold TH2, the current measurement value MVK that is outputted from the current measurement section 25c immediately after the temperature of the actuator section 15 reaching the temperature TE2 after being gradually increased, and for example, calculation using equation (3) above and the current measurement value MVK may be performed to calculate a current value corresponding to a predetermined temperature TE3, which is lower than the temperature TE2 by two to three degrees, and to acquire the calculated current value as the current threshold TH2. According to such an operation of the scan control section 25b, occurrence of a situation where the amplitude values of the drive signals are frequently switched due to output, from the current measurement section 25c, of the current measurement value MVK which changes at around the current threshold TH1 or TH2 may be prevented as much as possible, for example.

According to the present embodiment, the current threshold TH2 acquired at the time of manufacture of the scanning endoscope 2 does not have to be used as the threshold for detecting the current measurement value MVK, and the current threshold TH2 acquired at the time of use of the scanning endoscope 2 by a user may be used as the threshold for detecting the current measurement value MVK, for example. A specific operation for such a case will be described below. Note that in the following, for the sake of simplicity, a specific description of components and the like described above will be omitted as appropriate.

Before performing observation of an inside of a body cavity of a subject, a user instructs the controller 25 to start scanning by the scanning endoscope 2, by connecting each part of the scanning endoscope system 1 and turning on the power, and then, operating the scan start switch of the input device 5.

When the connector section 61 of scanning endoscope 2 and the connector receiving section 62 of the main body device 3 are connected, and the power of the main body device 3 is turned on, the scan control section 25b reads the control information stored in advance in the memory 24, and the current threshold TH1 stored in advance in the memory 16. Moreover, when detecting operation of the scan start switch of the input device 5, the scan control section 25b controls the signal generator 33 such that each of the drive signal DA of the amplitude value Ax1 and the drive signal DB of the amplitude value Ay1 is generated, based on the control information read from the memory 24.

After checking that scanning by the scanning endoscope 2 is started, the user inserts the insertion section 11 into the body cavity of the subject, and performs observation of a target object inside the body cavity. Then, in response to such an operation of the user, the temperature around the insertion section 11 of the scanning endoscope 2 is changed, and a size of the current measurement value MVK which is outputted from the current measurement section 25c is changed.

After detecting operation of the scan start switch of the input device 5, the scan control section 25b monitors the current measurement value MVK which is outputted from the current measurement section 25c according to supply of the drive signal DA of the amplitude value Ax1 and the drive signal DB of the amplitude value Ay1, while referring to the current threshold TH1 read from the memory 16.

When the current measurement value MVK is detected to have gradually increased and reached the current threshold TH1, the scan control section 25b amplifies each of the drive signals DA and DB to be supplied to the actuator section 15, by controlling the signal generator 33 such that the amplitude value of the drive signal DA is switched from Ax1 to Ax2 and the amplitude value of the drive signal DB is switched from Ay1 to Ay2.

The scan control section 25b acquires, as the current threshold TH2, the current measurement value MVK that is outputted from the current measurement section 25c at a timing immediately after first switching of the amplitude value of the drive signal DA from Ax1 to Ax2 after turning on of the power of the main body device 3 and first switching of the amplitude value of the drive signal DB from Ay1 to Ay2 after turning on of the power of the main body device 3.

Then, during a period of time when the power of the main body device 3 is turned on, the scan control section 25b switches the amplitude values of the drive signals DA and DB supplied to the actuator section 15, and switches the threshold for detecting the current measurement value MVK to the current threshold TH1 or TH2, according to the current measurement value MVK outputted from the current measurement section 25c, for example.

After completion of observation of the target object inside the body cavity by the scanning endoscope 2, the user performs an operation of removing the insertion section 11 from inside the body cavity of the subject, and performs an operation of switching the power of the main body device 3 from on to off.

At the time when the power of the main body device 3 is turned off, the scan control section 25b performs a process of discarding the current threshold TH2 which was used as the threshold for detecting the current measurement value MVK during the period of time when the power of the main body device 3 was on.

That is, according to the operation of the scan control section 25b as described above, a new current threshold TH2 is acquired every time observation of a target object inside a body cavity is performed by the scanning endoscope 2. Therefore, according to the operation of the scan control section 25b as described above, even if a property of the actuator section 15 is changed over time according to the number of times of use of the scanning endoscope 2, for example, an appropriate current threshold TH2 according to a current state of the actuator section 15 may be acquired.

As described above, according to the present embodiment, the amplitude value of the drive signal that is supplied to the actuator section 15 is discretely changed according to a change in the temperature of the actuator section 15, and switching between the current thresholds TH1 and TH2 to be used as the threshold for detecting the current measurement value MVK is performed at a timing of change of the amplitude value. Therefore, according to the present embodiment, reduction in an image quality caused by a change in a temperature of a usage environment of the scanning endoscope may be suppressed as much as possible.

Note that in the present embodiment, for example, in the case where the current measurement value outputted from the current measurement section 25c falls to or below a predetermined value, an operation of notifying a user of occurrence of malfunction regarding a swing state of the illumination fiber 12 may be performed.

The present invention is not limited to the embodiment described above, and various modifications and applications are possible within the range of the gist of the present invention.

What is claimed is:

1. A scanning endoscope system comprising:
    an optical fiber configured to guide illumination light supplied from a light source, and to emit the illumination light from an end portion;
    an actuator configured to shift an irradiation position of the illumination light emitted through the optical fiber, by swinging the end portion of the optical fiber; and
    a controller comprising hardware, the controller being configured to:
        generate and supply a drive signal for driving the actuator;
        measure, as a current measurement value, a current value of the drive signal supplied to the actuator; and
        perform a control such that an amplitude value of the drive signal is switched from a first amplitude value to a second amplitude value different from the first amplitude value, and switch a threshold for detecting the current measurement value from a first threshold to a second threshold different from the first threshold, when detecting that the current measurement value changes and reaches the first threshold.

2. The scanning endoscope system according to claim 1, wherein when detecting that the current measurement value increases and reaches the first threshold, the controller performs the control such that the amplitude value of the drive signal is switched from the first amplitude value to the second amplitude value greater than the first amplitude value, and switches the threshold for detecting the current measurement value from the first threshold to the second threshold greater than the first threshold.

3. The scanning endoscope system according to claim 2, wherein when detecting that the current measurement value decreases and reaches the second threshold, the controller performs the control such that the amplitude value of the drive signal is switched from the second amplitude value to the first amplitude value, and switches the threshold for detecting the current measurement value from the second threshold to the first threshold.

4. The scanning endoscope system according to claim 2, wherein the first threshold is a current value that is measured as the current measurement value at a timing when a temperature of the actuator supplied with the drive signal of the first amplitude value reaches a predetermined temperature.

5. The scanning endoscope system according to claim 2, wherein the second threshold is a current value that is measured as the current measurement value at a timing immediately after the amplitude value of the drive signal from the first amplitude value is switched to the second amplitude value.

6. The scanning endoscope system according to claim 5, wherein the second threshold is acquired while power of a main body device including the controller is on, and is stored in a memory provided in a scanning endoscope including the optical fiber and the actuator.

7. The scanning endoscope system according to claim 5, wherein the second threshold is acquired while power of a main body device including the controller is on, and is discarded when the power of the main body device is turned off.

8. The scanning endoscope system according to claim 1, wherein when detecting that an average value of respective current measurement values measured within a specific period of time changes and reaches the first threshold, the controller performs the control such that the amplitude value of the drive signal is switched from the first amplitude value to the second amplitude value, and switches the threshold for detecting the current measurement value from the first threshold to the second threshold.

\* \* \* \* \*